United States Patent
Miyake et al.

(10) Patent No.: US 11,838,644 B2
(45) Date of Patent: Dec. 5, 2023

(54) EXPOSURE RECORD TOTALIZER AND RADIOGRAPHY SYSTEM

(71) Applicant: Konica Minolta Inc., Tokyo (JP)

(72) Inventors: Nobuyuki Miyake, Yokohama (JP); Koutarou Kanamori, Hachioji (JP)

(73) Assignee: Konica Minolta, Inc., Tokyo (JP)

( * ) Notice: Subject to any disclaimer, the term of this patent is extended or adjusted under 35 U.S.C. 154(b) by 181 days.

(21) Appl. No.: 17/154,474

(22) Filed: Jan. 21, 2021

(65) Prior Publication Data

US 2021/0266445 A1 Aug. 26, 2021

(30) Foreign Application Priority Data

Feb. 21, 2020 (JP) .................................. 2020-028041

(51) Int. Cl.
  *H04N 23/73* (2023.01)
  *H04N 5/32* (2023.01)
  *G01T 1/29* (2006.01)
  *A61B 6/00* (2006.01)
  *G01T 1/02* (2006.01)

(52) U.S. Cl.
  CPC ........... *H04N 23/73* (2023.01); *A61B 6/5235* (2013.01); *A61B 6/542* (2013.01); *G01T 1/02* (2013.01); *G01T 1/2928* (2013.01); *H04N 5/32* (2013.01)

(58) Field of Classification Search
  CPC ......... A61B 6/5235; A61B 6/545; G01T 1/02; G01T 1/2928; H04N 5/2353; H04N 5/32
  See application file for complete search history.

(56) References Cited

U.S. PATENT DOCUMENTS

| | | | | |
|---|---|---|---|---|
| 5,315,631 | A * | 5/1994 | Hillen | H04N 5/32 378/62 |
| 6,205,347 | B1 * | 3/2001 | Morgan | A61B 6/037 600/407 |
| 2005/0169425 | A1 * | 8/2005 | Takasawa | A61B 6/542 378/97 |
| 2008/0123802 | A1 * | 5/2008 | Hirshenbein | G01N 23/04 378/5 |
| 2008/0292051 | A1 * | 11/2008 | Dippl | A61B 6/4283 378/97 |

(Continued)

FOREIGN PATENT DOCUMENTS

| JP | 2012-227822 A | 11/2012 |
|---|---|---|
| JP | 2019-126709 A | 8/2019 |
| JP | 2019-187942 A | 10/2019 |

OTHER PUBLICATIONS

Japanese Office Action (JPOA) dated Aug. 1, 2023 issued in Japanese Patent Application No. 2020-028041 and its English translation.

*Primary Examiner* — Blake C Riddick
(74) *Attorney, Agent, or Firm* — Rankin, Hill & Clark LLP

(57) ABSTRACT

An exposure record totalizer includes: a hardware processor that adds up a first exposure record of a first exposure image and a second exposure record of a second exposure image, when a radiography system generates the first exposure image through first exposure and the second exposure image through second exposure, and that links information about a third exposure record to a third exposure image generated on the basis of the first exposure image and the second exposure image, the third exposure record being generated by the hardware processor.

24 Claims, 5 Drawing Sheets

(56) References Cited

U.S. PATENT DOCUMENTS

| | | | |
|---|---|---|---|
| 2011/0054943 A1* | 3/2011 | Ohta | A61B 6/56 705/3 |
| 2013/0044865 A1* | 2/2013 | Kuwabara | G16H 20/40 378/98 |
| 2013/0051704 A1* | 2/2013 | Koishi | G06V 10/141 382/305 |
| 2013/0058453 A1* | 3/2013 | Kuwabara | H04N 5/32 378/97 |
| 2013/0058454 A1* | 3/2013 | Kuwabara | A61B 6/548 378/62 |
| 2013/0058455 A1* | 3/2013 | Kuwabara | A61B 6/545 378/97 |
| 2013/0058456 A1* | 3/2013 | Kuwabara | A61B 6/4233 378/97 |
| 2013/0058457 A1* | 3/2013 | Kuwabara | A61B 6/548 378/97 |
| 2013/0077744 A1* | 3/2013 | Kamiya | A61B 6/06 378/62 |
| 2013/0121464 A1* | 5/2013 | Tajima | A61B 6/548 378/97 |
| 2013/0148782 A1* | 6/2013 | Tajima | A61B 6/548 378/62 |
| 2013/0148784 A1* | 6/2013 | Tajima | A61B 6/4283 378/62 |
| 2013/0202086 A1* | 8/2013 | Tsuji | H01L 27/14605 378/62 |
| 2013/0208852 A1* | 8/2013 | Koishi | A61B 6/5288 378/19 |
| 2013/0208860 A1* | 8/2013 | Sugizaki | A61B 6/4233 378/62 |
| 2013/0223592 A1* | 8/2013 | Sato | A61B 6/542 378/97 |
| 2013/0259196 A1* | 10/2013 | Tajima | A61B 6/4283 250/394 |
| 2014/0056408 A1* | 2/2014 | Tajima | G01T 1/2018 378/116 |
| 2014/0064448 A1* | 3/2014 | Ito | A61B 6/542 378/97 |
| 2014/0072103 A1* | 3/2014 | Kitano | A61B 6/4233 378/62 |
| 2014/0086391 A1* | 3/2014 | Ohta | A61B 6/4233 378/91 |
| 2014/0177798 A1* | 6/2014 | Kitagawa | A61B 6/56 378/62 |
| 2014/0205066 A1* | 7/2014 | Kitagawa | A61B 6/542 378/62 |
| 2014/0211922 A1* | 7/2014 | Kuwabara | A61B 6/56 378/97 |
| 2014/0355739 A1* | 12/2014 | Kim | G06T 7/97 378/62 |
| 2015/0055752 A1* | 2/2015 | Takahashi | H05G 1/30 378/91 |
| 2015/0055753 A1* | 2/2015 | Tajima | A61B 6/4283 378/62 |
| 2015/0078528 A1* | 3/2015 | Okada | G01T 1/15 378/97 |
| 2015/0153464 A1* | 6/2015 | Imamura | A61B 6/58 378/207 |
| 2015/0164461 A1* | 6/2015 | Imamura | A61B 6/542 378/97 |
| 2015/0189194 A1* | 7/2015 | Tajima | H04N 5/32 378/62 |
| 2015/0192684 A1* | 7/2015 | Ito | G01T 1/20 250/361 R |
| 2015/0250440 A1* | 9/2015 | Sugahara | A61B 6/542 378/37 |
| 2015/0363926 A1* | 12/2015 | Enomoto | A61B 6/545 382/132 |
| 2016/0117823 A1* | 4/2016 | Isaacs | A61B 6/547 715/863 |
| 2017/0172535 A1* | 6/2017 | Kim | A61B 6/502 |
| 2017/0227475 A1* | 8/2017 | Shin | G01T 1/15 |
| 2018/0055473 A1* | 3/2018 | Torii | A61B 6/527 |
| 2018/0317872 A1* | 11/2018 | Kubota | A61B 6/46 |
| 2019/0223822 A1* | 7/2019 | Takagi | A61B 6/5211 |

* cited by examiner

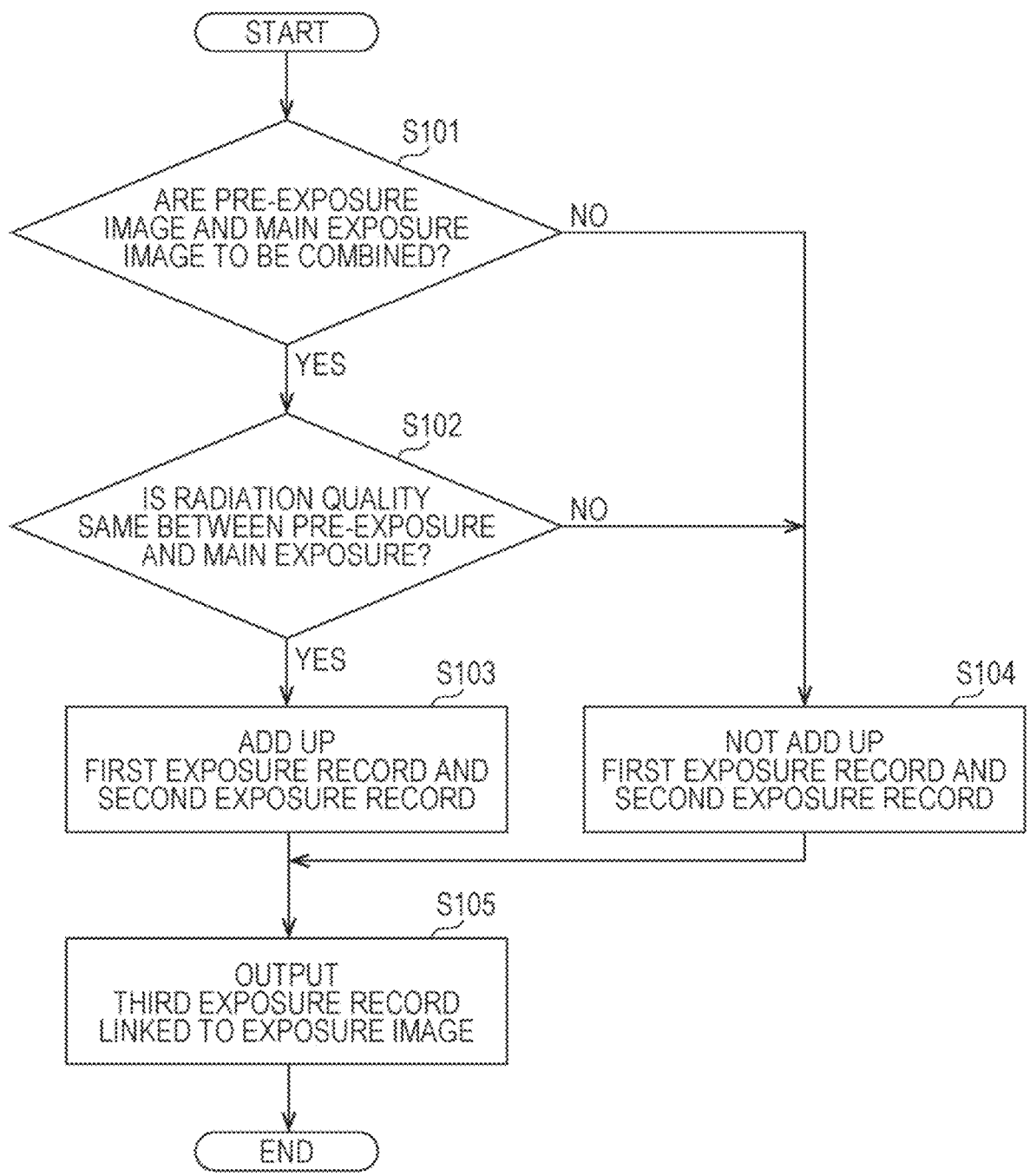

EXPOSURE RECORD TOTALIZER AND RADIOGRAPHY SYSTEM

The entire disclosure of Japanese patent Application No. 2020-028041, filed on Feb. 21, 2020, is incorporated herein by reference in its entirety.

BACKGROUND

Technological Field

The present invention relates to an exposure record totalizer and a radiography system.

Description of the Related Art

When capturing a radiological image, a conventional radiography system performs a plurality of exposure processes including first exposure and second exposure, having an automatic exposure control function or the like for performing main exposure and performing pre-exposure prior to the main exposure. For example, the automatic exposure control function performs the pre-exposure with a lower radiation dose than that for the main exposure, and determines imaging conditions such as the radiation dose for the main exposure, on the basis of the obtained pre-exposure image and the accompanying information (the irradiation time in the pre-exposure, for example) linked to the pre-exposure image.

For example, JP 2019-126709 A discloses a configuration that determines, from image analysis of a pre-exposure image, whether the pre-exposure image has been captured appropriately. By this technique, an exposure image that is a combination of the pre-exposure image and a main exposure image is generated.

As a technique for combining images. JP 2012-227822 A also discloses a technique for generating a combined image by combining images at a predetermined combining ratio, the images having been captured under different exposure conditions.

A radiography system normally acquires record values of actual exposure records (the tube voltage, the tube current, and the irradiation, or the tube voltage and the tube current time product, for example) every time completing exposure of the object to radiation, and then performs saving, display, and the like on a console or the like.

In a case where exposure images are managed by the console, the above mentioned actual values are linked to exposure images and are then saved, or are output to an external device or the like. In the above configuration that performs exposure a plurality of times, the exposure image of first exposure to which the exposure record of the first exposure is linked, and the exposure image of second exposure to which the exposure record of the second exposure is linked are saved, displayed, and managed, for example.

However, in a case where a combined image is generated from two exposure images as in the configuration disclosed in JP 2019-126709 A, if each exposure record linked to each corresponding exposure image is managed as in conventional cases, there is a possibility that inconvenience will be caused to the user in saving and displaying the combined image, and in linking each exposure record to the combined image. For example, if two exposure records are linked to one combined image, the user might wrongly recognize that one of the two exposure records is the exposure record of the combined image.

Meanwhile, the configuration disclosed in JP 2012-227822 A is not a configuration that links radiation exposure records to combined images, and therefore, is incapable of solving the above problem

SUMMARY

An object of the present invention is to provide an exposure record totalizer and a radiography system that are capable of appropriately linking exposure records to exposure images.

To achieve the abovementioned object, according to an aspect of the present invention, an exposure record totalizer reflecting one aspect of the present invention comprises: a hardware processor that adds up a first exposure record of a first exposure image and a second exposure record of a second exposure image, when a radiography system generates the first exposure image through first exposure and the second exposure image through second exposure, and that links information about a third exposure record to a third exposure image generated on the basis of the first exposure image and the second exposure image, the third exposure record being generated by the hardware processor.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention:

FIG. 7 is a flowchart showing an example operation of exposure record output control in a control unit.

DETAILED DESCRIPTION OF EMBODIMENTS

Figure 1:
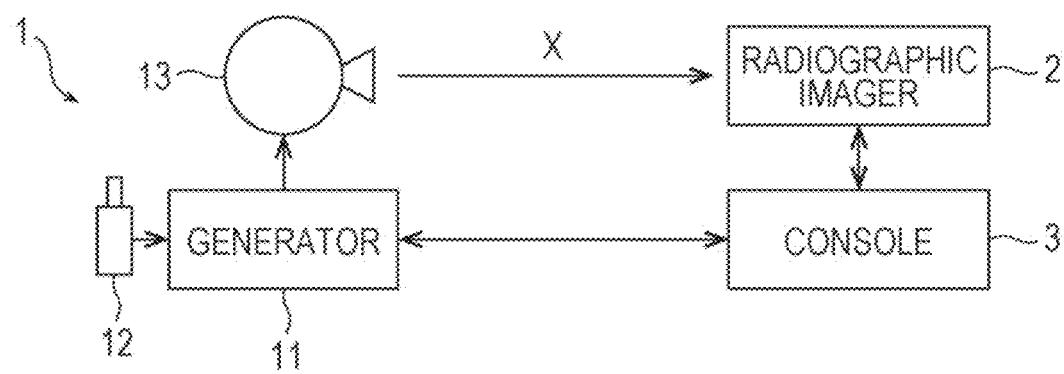
FIG. 1 is a block diagram showing the configuration of a radiography system according to an embodiment of the present invention.

Hereinafter, one or more embodiments of the present invention will be described with reference to the drawings. However, the scope of the invention is not limited to the disclosed embodiments. FIG. 1 is a block diagram showing a configuration of a radiography system 100 according to an embodiment of the present invention.

As shown in FIG. 1, the radiography system 100 according to this embodiment includes an irradiator 1, a radiographic imager 2, and a console 3. The radiography system 100 can be connected to a radiology information system (RIS) and a picture archiving and communication system (PACS) that are not shown in the drawing.

The irradiator 1 is connected to the console 3 so as to be able to communicate in a wired or wireless manner. Further, the irradiator 1 includes a generator 11, an exposure switch 12, and a radiation source 13.

The generator 11 is designed to be capable of applying a voltage to the radiation source 13 in accordance with preset radiation exposure conditions (tube voltage, tube current, irradiation time, tube current time product (mAs value), and the like), with the trigger being the exposure switch 12 being operated.

The radiation source 13 (a tube) includes a rotating anode, a filament, and the like that are not shown. When a voltage is applied from the generator 11, the filament irradiates the rotating anode with an electron beam corresponding to the applied voltage, and the rotating anode then emits radiation X (X-rays or the like) corresponding to the intensity of the electron beam.

Although the generator 11, the exposure switch 12, and the radiation source 13 are separate components in the example shown in FIG. 1, these components may be integrally formed. Further, although the exposure switch 12 is connected to the generator 11 in the example shown in FIG. 1, the exposure switch 12 may be provided in another device. Alternatively, the irradiator 1 may be installed in the photographing room, or may be incorporated into a visiting car or the like so as to be movable.

The radiographic imager 2 is connected to the console 3 so as to be able to communicate in a wired or wireless manner. The radiographic imager 2 is also designed to be able to generate image data of an exposure image of an object by being exposed to the radiation X from the irradiator 1 via the object.

Figure 2:
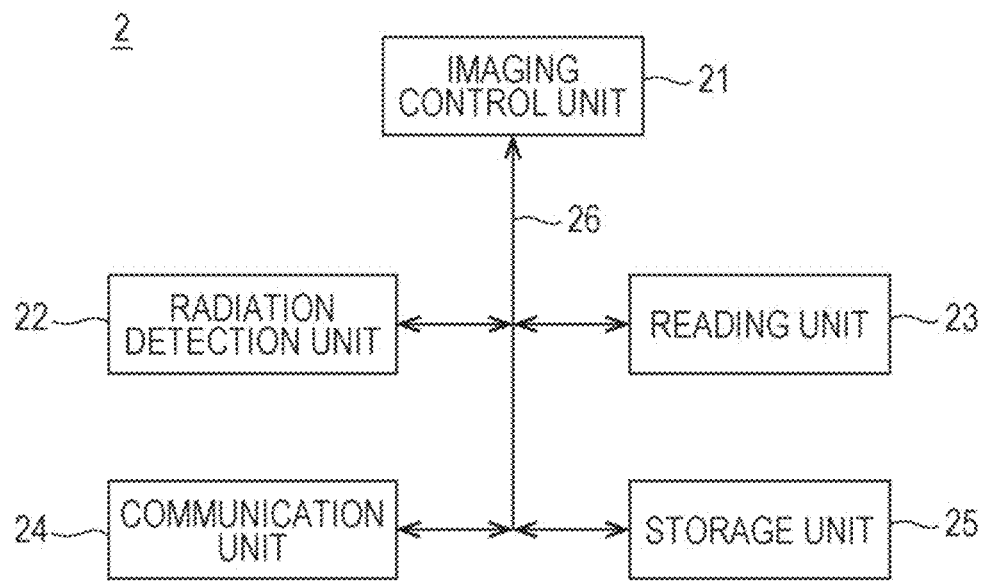
FIG. 2 is a block diagram showing the specific configuration of a radiographic imager.

As shown in FIG. 2, the radiographic imager 2 includes an imaging control unit 21, a radiation detection unit 22, a reading unit 23, a communication unit 24, a storage unit 25, and a bus 26 connecting these components to one another.

The imaging control unit 21 is formed with a central processing unit (CPU), a random access memory (RAM), and the like. The CPU of the imaging control unit 21 reads various programs stored in the storage unit 25 on the basis of a control signal or the like received from an external device such as the console 3, loads the programs into the RAM, performs various processes according to the loaded programs, and centrally controls operations of the respective components in the radiographic imager 2.

The radiation detection unit 22 is formed with a substrate in which pixels each including a radiation detection element that generates an electric charge corresponding to the dose of received radiation X and a switch element are arranged in a two-dimensional pattern (a matrix-like pattern).

The reading unit 23 is designed to be capable of reading the amount of electric charge emitted from each pixel as a signal value, and generating image data from a plurality of signal values.

The communication unit 24 is designed to be capable of receiving various control signals, various kinds of data, and the like from external devices, and transmitting various control signals, generated image data, and the like to external devices.

The storage unit 25 is formed with a nonvolatile semiconductor memory, a hard disk, or the like, and stores the various programs to be executed by the imaging control unit 21 and the parameters and the like necessary for executing processes according to the programs. The storage unit 25 can also store image data generated by the reading unit 23 and various kinds of data processed by the imaging control unit 21.

In the radiographic imager 2 designed in this manner, when the imaging control unit 21 is exposed to radiation with each switch element of the radiation detection unit 22 turned off, electric charge according to the dose of radiation is stored into each pixel. When the imaging control unit 21 turns on each switch element and releases the electric charge from each pixel, the reading unit 23 converts each charge amount into a signal value, and reads the signal values as image data.

The radiographic imager 2 may include a scintillator or the like therein, convert the emitted radiation X into light of another wavelength such as visible light with the scintillator, and generate electric charge corresponding to the converted light. Alternatively, the radiographic imager 2 may generate electric charge directly from the radiation X, without a scintillator or the like. Further, the radiographic imager 2 may be a dedicated machine integrated with an imaging table, or may be of a portable type.

The console 3 is formed with a PC, a mobile terminal, or a dedicated device, and is connected to the irradiator 1, the radiographic imager 2, and the like so as to be communicate in a wired or wireless manner. The console 3 is capable of setting imaging conditions and an imaging target site for the irradiator 1 and the radiographic imager 2, on the basis of an imaging order from an external device (a RIS or the like) or an operation by the user. The console 3 corresponds to the "exposure record totalizer" according to an embodiment of the present invention.

Figure 3:
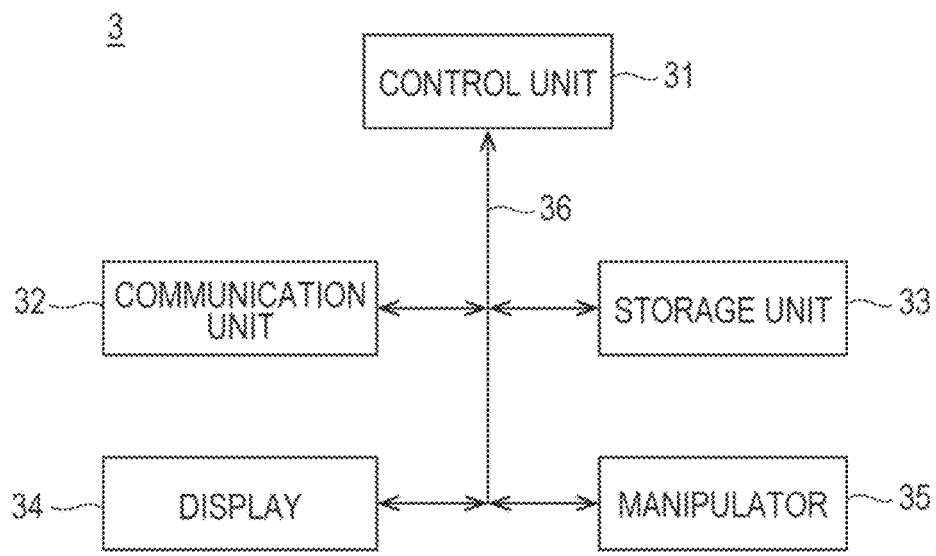
FIG. 3 is a block diagram showing the specific configuration of a console.

As shown in FIG. 3, the console 3 includes a control unit 31, a communication unit 32, a storage unit 33, a display 34, a manipulator 35, and a bus 36 connecting these components to one another.

The control unit 31 is formed with a CPU, RAM, and the like. The CPU of the control unit 31 reads various programs stored in the storage unit 33 in accordance with operations of the manipulator 35, loads the programs into the RAM, performs various processes according to the loaded programs, and centrally controls operations of the respective components in the console 3.

The communication unit 32 includes a LAN adapter, a modem, a terminal adapter (TA), and the like, and controls data transmission/reception with each device connected to the communication network.

The storage unit 33 is formed with a nonvolatile semiconductor memory, a hard disk, or the like, and stores the various programs to be executed by the control unit 31 and the parameters and the like necessary for executing processes according to the programs. The storage unit 33 can also link store image data received from the radiographic imager 2 and image data processed by the control unit 31 to accompanying information, and store the image data.

The display 34 is formed with a monitor such as a liquid crystal display (LCD) or a cathode ray tube (CRT), and displays an input instruction from the manipulator 35, data, and the like, in accordance with an instruction indicated by a display signal input from the control unit 31.

The manipulator 35 includes a keyboard having cursor keys, numerical input keys, various function keys, and the like, and a pointing device such as a mouse, and outputs an instruction signal input by a key operation performed on the keyboard or by a mouse operation, to the control unit 31. The manipulator 35 may also include a touch panel on the display screen of the display 34. In this case, the manipulator 35 outputs an instruction signal input via the touch panel, to the control unit 31.

Next, control on the radiography system 100 by the control unit 31 is described. The control unit 31 performs automatic exposure control to determine the imaging conditions for main exposure (second exposure) on the basis of a pre-exposure image obtained by pre-exposure (first exposure) and accompanying information linked to the pre-exposure image. The pre-exposure is performed prior to the main exposure, with a lower dose than that in the main exposure.

When performing the automatic exposure control, the control unit 31 generates a pre-exposure image (a first exposure image) through pre-exposure and a main exposure image (a second exposure image) through main exposure, and combines the pre-exposure image and the main exposure image. The control unit 31 links a first exposure record of the pre-exposure to the pre-exposure image, and stores the first exposure record and the pre-exposure image into the storage unit 33. The control unit 31 also links a second exposure record of the main exposure to the main exposure image, and stores the second exposure record and the main exposure image into the storage unit 33.

The first exposure record is the exposure record of the radiography system 100 when the pre-exposure image is generated, and includes radiation records, such as the tube voltage, the tube current, the irradiation time, the tube current time product (the product of the tube current and the irradiation time), and the dose of radiation (the area dose value and the incident surface dose value). The second exposure record is the exposure record of the radiography system 100 when the main exposure image is generated, and includes radiation records, such as the tube voltage, the tube current, the irradiation time, the tube current time product, and the dose of radiation.

When generating the pre-exposure image and the main exposure image, the control unit 31 adds up the first exposure record and the second exposure record. The control unit 31 corresponds to the "totalizer" according to an embodiment of the present invention.

Specifically, when combining the pre-exposure image and the main exposure image, the control unit 31 determines whether to add up the first exposure record and the second exposure record, depending on whether the radiation quality differs between the first exposure and the second exposure.

In a case where the radiation quality is the same between the first exposure and the second exposure, and the first exposure record and the second exposure record are at least one of the records of the irradiation time, the tube current time product, and the dose of radiation, the control unit 31 determines to add up the first exposure record and the second exposure record. Further, in a case where the radiation quality is the same between the first exposure and the second exposure, and the first exposure record and the second exposure record are at least one of the records of the tube voltage and the tube current of radiation, the control unit 31 determines not to add up the first exposure record and the second exposure record.

Further, in a case where the radiation quality is different between the first exposure and the second exposure, the control unit 31 determines not to add up the first exposure record and the second exposure record.

A case where the radiation quality is the same is a case where the tube voltage of radiation is the same, for example. A case where the radiation quality is different is a case where the tube voltage of radiation is different, for example.

The control unit 31 links information about a third exposure record based on a result of determination as to whether to add up the first exposure record and the second exposure record, to the exposure image (a third exposure image) generated on the basis of the pre-exposure image and the main exposure image, and outputs the exposure image and the information to at least one of the devices such as the storage unit 33, the display 34, and an external device. The control unit 31 corresponds to the "linker" according to an embodiment of the present invention. The external device is a device located outside the radiography system 100, and may be the above described RIS or PACS, an image detector, a management device such as an exposure dose management system, a display device, a storage device, or the like, for example.

In a case where the control unit 31 determines to add up the first exposure record and the second exposure record, the control unit 31 regards the exposure record that is the sum of the first exposure record and the second exposure record as the third exposure record. That is, the third exposure record that is the sum of the first exposure record and the second exposure record is linked to the combined exposure image obtained by combining the pre-exposure image and the main exposure image.

Further, in a case where the control unit 31 determines not to add up the first exposure record and the second exposure record, and uses the main exposure image as the exposure image, the control unit 31 regards the second exposure record as the third exposure record. That is, the second exposure record (the third exposure record) is linked to the main exposure image.

Further, in a case where the control unit 31 determines not to add up the first exposure record and the second exposure record, and uses the combined exposure image as the exposure image, the control unit 31 regards both the first exposure record and the second exposure record as the third exposure record. That is, the first exposure record and the second exposure record are both linked to the combined exposure image.

The storage unit 33 stores the third exposure record linked to the above exposure image, and the display 34 displays the above exposure image and the third exposure record linked to the exposure image. Also, the third exposure record linked to the above exposure image is output to the external device.

In an example case, the pre-exposure image and the main exposure image are combined, the first exposure record of the pre-exposure indicates a tube voltage of 120 kV a tube current of 100 mA, and an irradiation time of 4 msec, and the second exposure record of the main exposure indicates a tube voltage of 120 kV, a tube current of 100 mA, and an irradiation time of 16 msec.

In this case, the tube voltages and tube currents indicate the values per hour. Therefore, the values that are used in the pre-exposure and the main exposure, instead of being added up, are set as the third exposure record.

Moreover, as the tube voltage is the same between the pre-exposure and the main exposure, the radiation quality is the same. Therefore, as for the irradiation time, the time obtained by adding up the irradiation time in the pre-exposure and the irradiation time in the main exposure is regarded as the third exposure record. Accordingly, the irradiation time according to the third exposure record is 20 msec, which is the sum of the irradiation time of 4 msec in the pre-exposure and the irradiation time of 16 msec in the main exposure.

Figure 4:
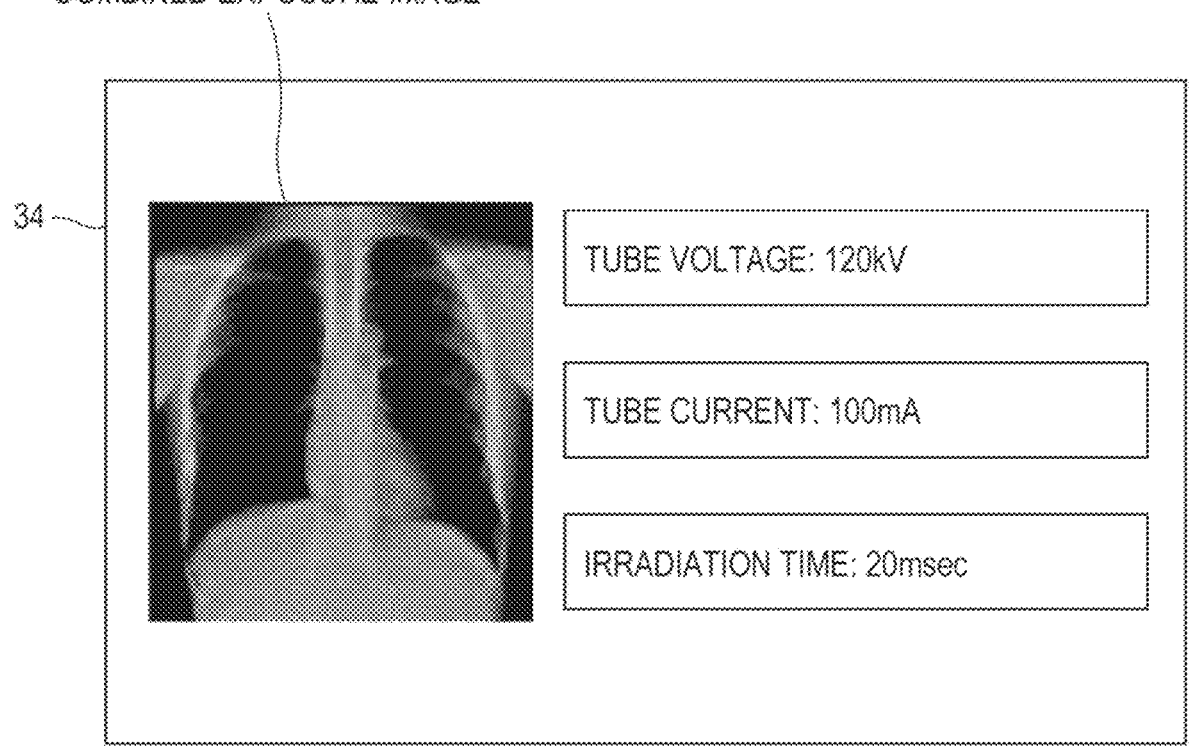
FIG. 4 is a diagram showing an example indication displayed on a display.

As shown in FIG. 4, the display 34 displays the combined exposure image obtained by combining the pre-exposure image and the main exposure image, a tube voltage of 120 kV a tube current of 100 mA, and an irradiation time of 20 msec, for example. FIG. 4 shows an example in which the tube voltage and the tube current are the same between the pre-exposure and the main exposure, and therefore, the display does not indicate any distinction between the pre-exposure and the main exposure.

As the display 34 displays the combined exposure image and the third exposure record linked to each other as described above, the user can easily recognize the third exposure record while checking the combined exposure image. Also, as the third exposure record, which is the sum of the first exposure record of the pre-exposure and the second exposure record of the main exposure, is displayed, the user does not need to perform calculation to recognize the exposure records required for the combined exposure image, and thus, the burden on the user can be reduced.

Further, in FIG. 4, in a case where the display 34 displays the combined exposure image, the combined exposure image and the third exposure record are displayed, without the pre-exposure image and the main exposure image being displayed. With this arrangement, it is possible to prevent the user from erroneously recognizing that the third exposure record is linked to the pre-exposure image or the main exposure image.

In an example case, the pre-exposure image and the main exposure image are combined, the first exposure record of the pre-exposure indicates a tube voltage of 120 kV, a tube current of 50 mA, and an irradiation time of 8 msec, and the second exposure record of the main exposure indicates a tube voltage of 120 kV, a tube current of 100 mA, and an irradiation time of 16 msec.

In this case, the tube voltages and the tube currents in the pre-exposure and the main exposure are not added up either, and the values used in the pre-exposure and the main exposure are set as the third exposure record.

In this case, the tube voltage is the same between the pre-exposure and the main exposure, and accordingly, the radiation quality is the same. However, the tube current differs between the pre-exposure and the main exposure, and therefore, the irradiation times in the pre-exposure and the main exposure cannot be added up in a simple manner.

Because of this, the tube current time product, which is the product of the tube current and the irradiation time, is used in place of the exposure record of the tube current and the irradiation time in this case. The tube current time product according to the third exposure record is 2 mAs, which is the sum of the tube current time product of 50 mA×8 msec in the pre-exposure, and the tube current time product of 100 mA×16 msec in the main exposure.

Meanwhile, in a case where there are two different tube currents for one exposure image, some systems for managing exposure images and tube currents cannot accept two tube currents for one exposure image. Therefore, in such a case, the tube current time product is linked to the combined exposure image as above, so that the third exposure record can be accurately managed.

All of the tube voltage, the tube current in the pre-exposure, the tube current in the main exposure, and the tube current time product obtained by adding up the values in the pre-exposure and the main exposure may be linked to the combined exposure image, and be output to the storage unit 33, the display 34, and the external device. Alternatively, the tube voltage and the tube current time product may be linked to the combined exposure image, and be output to the storage unit 33, the display 34, and the external device.

Even in a case where there are two tube currents as described above, some users might wish to conduct management on the basis of irradiation times. For example, in a case where management is conducted on the basis of tube current time products though the user wishes to recognize irradiation times to understand the influence of irradiation times on body movement of the object, the user cannot recognize the irradiation times.

Figure 5:
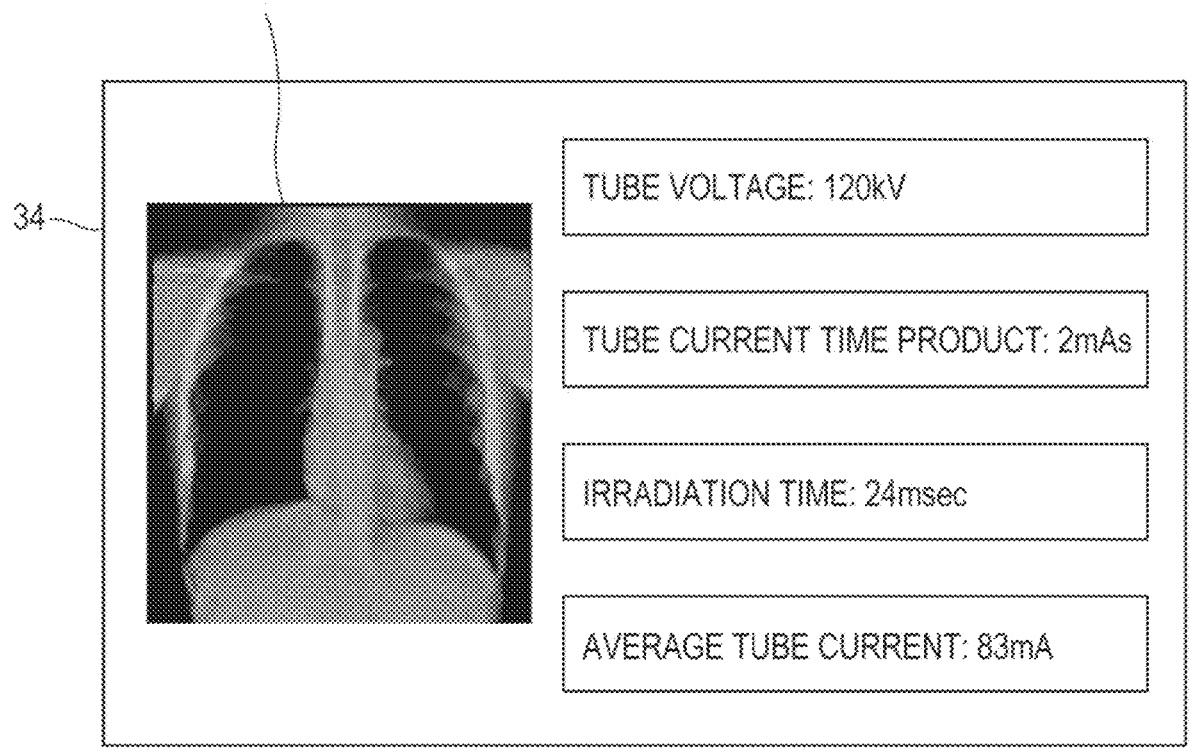
FIG. 5 is a diagram showing an example indication displayed on a display.

In this case, as shown in FIG. 5, an irradiation time of 24 msec, which is the sum of the irradiation time of 8 msec in the pre-exposure, and the irradiation time of 16 msec in the main exposure, is linked to the combined exposure image, for example. Also, the average tube current obtained by averaging the tube current in the pre-exposure and the tube current in the main exposure may be linked to the combined exposure image. In this case, the value obtained by dividing the tube current time product by the irradiation time (2 mAs/24 msec=83 mA) is linked to the combined exposure image.

In an example case, the pre-exposure image and the main exposure image are combined, the first exposure record of the pre-exposure indicates a tube voltage of 110 kV, a tube current of 50 mA, and an irradiation time of 8 msec, and the second exposure record of the main exposure indicates a tube voltage of 120 kV, a tube current of 100 mA, and an irradiation time of 16 msec.

In this case, the tube voltage differs between the pre-exposure and the main exposure, and therefore, the radiation quality in the pre-exposure differs from the radiation quality in the main exposure. Because of this, if the irradiation times and the tube current time products in the pre-exposure and the main exposure are added up, it will be difficult to accurately manage the exposure. In this case, the third exposure record is not the sum of the first exposure record and the second exposure record, but both the first exposure record and the second exposure record.

Therefore, in this case, both the first exposure record and the second exposure record are linked to the combined exposure image.

With this arrangement, however, the number of display items on the display 34 becomes larger, and usability might deteriorate. Therefore, the tube current time product in the pre-exposure and the tube current time product in the main exposure may be output to the storage unit 33, the display 34, and the like.

There also are cases where the added filter in the irradiator 1 may differ between the pre-exposure and the main exposure. If the added filter differs between the pre-exposure and the main exposure, the radiation quality in the pre-exposure and the radiation quality in the main exposure will be different. Therefore, in this case, the third exposure record is both the first exposure record and the second exposure record, and both the first exposure record and the second exposure record are linked to the combined exposure image.

Further, in a case where the exposure records include radiation doses such as area doses and incident surface doses, the area doses and the incident surface doses may be set as the conditions for adding up the values in the pre-exposure and the values in the main exposure. The area dose may be a value measured by an area dosimeter provided in one of the devices of the radiography system 100, or may be a value calculated depending on the tube voltage, the tube current, the irradiation time, the irradiation field, the presence/absence of an added filter, and the type of the added filter.

In a case where the exposure records include exposure index (EI) values and sensitivity index values (S values), if the EI value and the S value of the pre-exposure or the EI value and the S value of the main exposure are linked to the combined exposure image, it will become impossible to appropriately manage the reached dose of radiation. However, there are cases where the EI values and the S values in the pre-exposure and the main exposure cannot be added in a simple manner. Therefore, in a case where the exposure records include EI values and S values, the EI values and the S values in the pre-exposure and the main exposure are not added up, but an EI value and an S value are calculated from the combined exposure image.

In a case where the third exposure record is linked to the combined exposure image and is output to the external device, the first exposure record of the pre-exposure and the second exposure record of the main exposure are preferably not linked to the combined exposure image before being output. This is because, if the first exposure record and the second exposure record are not appropriately handled by the external device, there is a possibility that the exposure dose of the object (patient) will not be appropriately managed. An example case where the exposure dose will not be appropriately managed is a case where the third exposure record and the second exposure record are erroneously added up.

The control unit 31 may also select combining exposure to combine the pre-exposure image and the main exposure image into an exposure image (the third exposure image), or non-combining exposure to set the main exposure image as an exposure image (the third exposure image) without combining the pre-exposure image and the main exposure image. The control unit 31 corresponds to the "selector" according to an embodiment of the present invention.

Specifically, the control unit 31 selects either the combining exposure or the non-combining exposure, on the basis of information about body movement of the object of the radiography system 100.

The presence/absence of body movement of the object is determined on the basis of the time interval between the pre-exposure and the main exposure, for example. The time interval between the pre-exposure and the main exposure may be prolonged due to a delay in the transfer time of the pre-exposure image or the like. It is believed that, if the time interval is prolonged, body movement of the object will become larger.

Therefore, in a case where the time interval between the pre-exposure and the main exposure increases by a certain amount, the control unit 31 selects the non-combining exposure. In the case of the non-combining exposure, or in a case where the pre-exposure image and the main exposure image are not to be combined, the control unit 31 determines not to add up the first exposure record and the second exposure record.

The control unit 31 then sets the second exposure record, which is the exposure record of the main exposure image, as the third exposure record, for example. With this arrangement, even in a case where the combined exposure image is not an appropriate image, the main exposure image can be used instead.

Alternatively, the presence/absence of body movement of the object may be determined on the basis of the mismatch between the pre-exposure image and the main exposure image, for example. The pre-exposure image and the main exposure image are superimposed on each other, for example, so that the mismatch between the pre-exposure image and the main exposure image can be determined. In a case where this mismatch is so large that the pre-exposure image and the main exposure image cannot be combined, body movement of the object can be determined to be large.

Therefore, the control unit 31 selects the non-combining exposure, when the mismatch between the pre-exposure image and the main exposure image increases by a certain amount. With this arrangement, even in a case where the combined exposure image is not an appropriate image, the main exposure image can be used instead.

Further, the control unit 31 may select either the combining exposure or the non-combining exposure, on the basis of a selection command from the manipulator 35. The manipulator 35 outputs a selection command for either the combining exposure or the non-combining exposure to the control unit 31, on the basis of the users operation.

Figure 6:
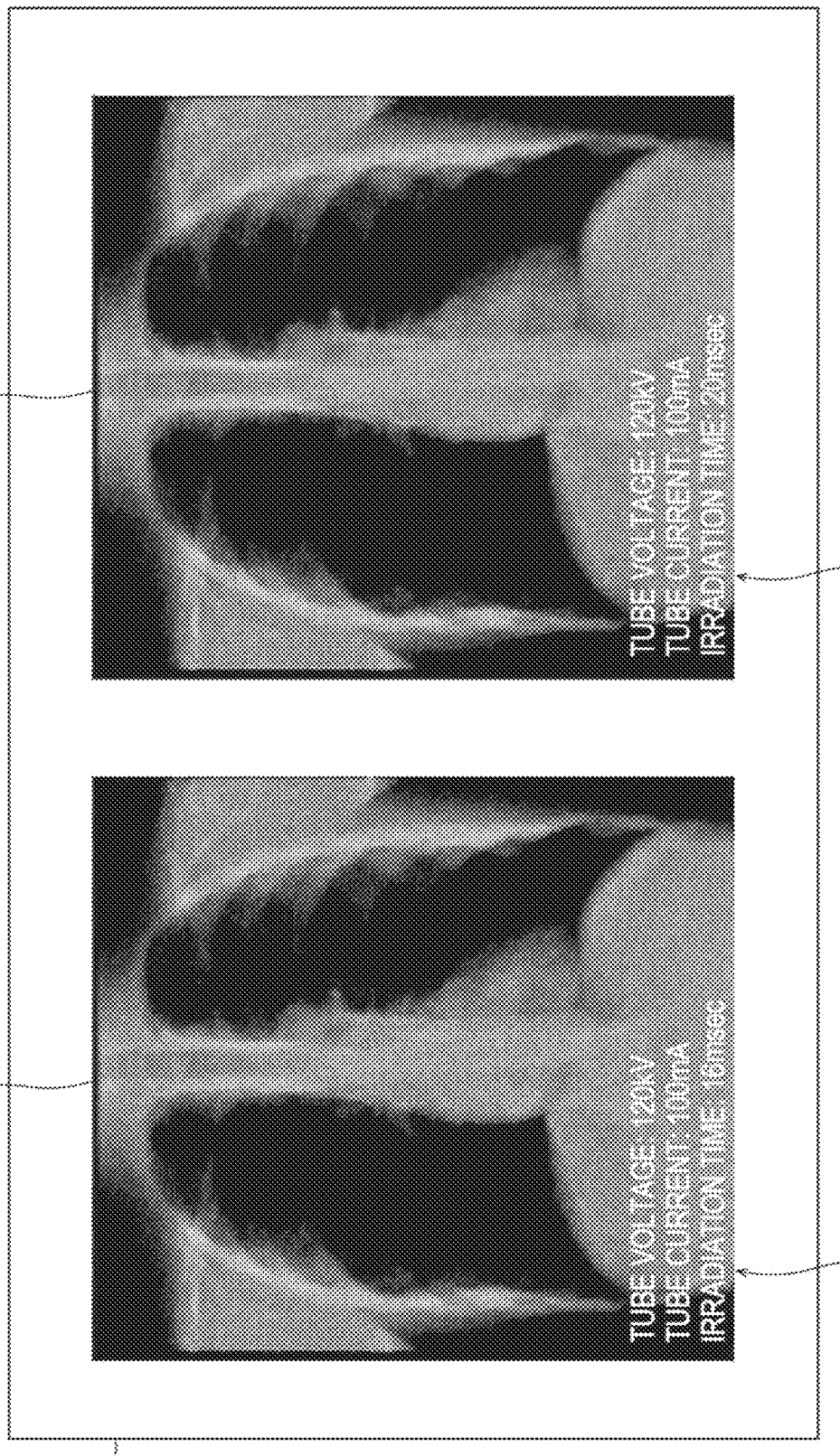
FIG. 6 is a diagram showing an example indication displayed on a display.

For example, the manipulator 35 has a button for selecting either the combining exposure or the non-combining exposure, so that the user can select either the combining exposure or the non-combining exposure. For example, as shown in FIG. 6, the display 34 simultaneously displays the combined exposure image obtained by combining the pre-exposure image and the main exposure image, and the main exposure image.

With this arrangement, the user can easily compare the combined exposure image with the main exposure image.

The display 34 may also display information based on the third exposure record and information based on the second exposure record, while simultaneously displaying the combined exposure image and the main exposure image. FIG. 6 shows an example in which the third exposure record and the second exposure record are the tube voltages, the tube currents, and the irradiation times. FIG. 6 also shows an example in which the third exposure record and the second exposure record are superimposed on the combined exposure image and the main exposure image, respectively. Further, although not shown in the drawing. S values and EI values may be included in the third exposure record and the second exposure record. That is, an S value and an EI value calculated from the combined exposure image as described above are superimposed on the combined exposure image, and an S value and an EI value calculated from the main exposure image are superimposed on the main exposure image.

With this arrangement, the user can easily compare the combined exposure image with the main exposure image, while comparing exposure records.

In a case where the main exposure image is selected by the control unit 31, and the second exposure record is linked to the main exposure image and is output, the display 34 displays the main exposure image and the second exposure record in the same manner as in FIG. 4, FIG. 5, or the like. In other words, when displaying the main exposure image, the display 34 displays the main exposure image and the second exposure record, while not displaying the pre-exposure image and the combined exposure image.

As the display 34 displays the main exposure image and the second exposure record linked to each other as described above, the user can easily recognize the second exposure record while checking the main exposure image.

An example operation of exposure record output control in the control unit 31 designed as described above is now described. FIG. 7 is a flowchart showing an example operation of exposure record output control in the control unit 31. The process shown in FIG. 7 is performed as appropriate when capturing of an exposure image is completed in the radiography system 100, for example.

As shown in FIG. 7, the control unit 31 determines whether to combine the pre-exposure image and the main exposure image (step S101). If the result of the determination shows that the pre-exposure image and the main exposure image are not to be combined (step S101, NO), the process moves on to step S104.

If the pre-exposure image and the main exposure image are to be combined (step S101, YES), on the other hand, the control unit 31 determines whether the radiation quality is the same between the pre-exposure and the main exposure (step S102).

If the result of the determination shows that the radiation quality differs between the pre-exposure and the main exposure (step S102, NO), the process moves onto step S104. If the radiation quality is the same between the pre-exposure and the main exposure (step S102, YES), on the other hand, the control unit 31 adds up the first exposure record and the second exposure record, to generate the third exposure record (step S103).

If the result of step S101 is NO, or the result of step S102 is NO, the control unit 31 does not add up the first exposure record and the second exposure record (step S104). Specifically, if the result of step S101 is NO, the second exposure record of the main exposure image is set as the third exposure record. If the result of step S102 is NO, both the first exposure record of the pre-exposure image and the second exposure record of the main exposure image are set as the third exposure record.

After step S103 or step S104, the control unit 31 outputs the third exposure record linked to the exposure image (step S105). Ina case where step S105 is carried out immediately after step S103, the exposure image is the combined exposure image obtained by combining the pre-exposure image and the main exposure image. In a case where step S105 is carried out immediately after step S104, and the result of step S101 is NO, the exposure image is the main exposure image. In a case where step S105 is carried out immediately after step S104, and the result of step S102 is NO, the exposure image is the combined exposure image. After step S105, this control operation comes to an end.

According to this embodiment designed as described above, in a case where the pre-exposure image and the main exposure image are combined, the third exposure record, which is the sum of the first exposure record and the second exposure record, is linked to the combined exposure image and is output, under predetermined conditions. As a result, the combined exposure image and the third exposure record can be appropriately linked to each other.

In a case where the radiation quality is the same between the pre-exposure and the main exposure, the first exposure record and the second exposure record are added up. Thus, the combined exposure image and the third exposure record that are appropriately linked to each other can be managed.

In a case where the radiation quality differs between the pre-exposure and the main exposure, the first exposure record and the second exposure record are not added up. Thus, management of the combined exposure image and the third exposure record in an inappropriate state can be prevented.

In a case where the pre-exposure image and the main exposure image are not combined due to body movement of the object, mismatch between the pre-exposure image and the main exposure image, or the like, the first exposure record and the second exposure record are added up, and the main exposure image and the second exposure record (the third exposure record) are output. Thus, the main exposure image can be used in a case where the main exposure image is more appropriate than the combined exposure image. Further, the third exposure record, which is the second exposure record, is linked to the main exposure image, so that the exposure record and the exposure image can be appropriately linked to each other.

In other words, it is possible to appropriately associate the exposure image to be output and displayed with the exposure record that has contributed to the exposure image, depending on whether to combine images, and whether the radiation quality differs. Thus, the user can appropriately manage the exposure record of each exposure image.

In the above embodiment, the combining exposure or the non-combining exposure can be selected. However, embodiments of the present invention are not limited to this. For example, a first exposure image and a second exposure image may be generated, and either the first exposure image or the second exposure image may be used.

In this case, the control unit 31 determines not to add up the first exposure record of the first exposure image and the second exposure record of the second exposure image. The control unit 31 links the exposure record of the first exposure image or the second exposure image, whichever is to be used as the exposure image, as the third exposure record to the exposure image, and outputs the exposure record and the exposure image.

In the above embodiment, the control unit 31 determines whether to add up the first exposure record and the second exposure record, depending on whether the radiation quality differs between the pre-exposure and the main exposure. However, embodiments of the present invention are not limited to this. For example, the control unit 31 may determine whether to add up the first exposure record and the second exposure record, depending on whether the pre-exposure image and the main exposure image are combined.

Further, in the above embodiment, to determine whether the radiation quality differs between the first exposure and the second exposure, the tube voltage included in the first exposure record and the tube voltage included in the second exposure record are compared with each other. However, embodiments of the present invention are not limited to this. For example, instead of the tube voltage included in the first exposure record, the tube voltage included in the imaging conditions for the first exposure may be used. Also, instead of the tube voltage included in the second exposure record, the tube voltage included in the imaging conditions for the second exposure may be used. Further, the record of the added filter used in each exposure process may also be used in determining the difference in radiation quality from the difference between the added filter used in the first exposure and the added filter used in the second exposure. However, the added filter information included in the imaging conditions for the first exposure and the imaging conditions for the second exposure may also be used.

In a case where the tube voltage included in the first exposure record and the tube voltage included in the second exposure record are compared with each other in determining whether the radiation quality differs between the first exposure and the second exposure, if the difference between the two tube voltages is very small, the radiation quality may be considered to be the same. For example, even if the tube voltage under the imaging conditions for the first exposure and the tube voltage under the imaging conditions for the second exposure are both 120 kV, the actual records might deviate from the target. In that case, the tube voltage included in the first exposure record might be 121 kV, and the tube voltage included in the second exposure record might be 119 kV, for example. In this case, many users think that it will be easier to recognize and manage the exposure records if both radiation qualities are the same. Therefore, if the difference is very small, the radiation quality in the first exposure and the radiation quality in the second exposure are considered to be the same. Specifically, in a case where the absolute value of the difference in tube voltage between the first exposure and the second exposure is equal to or smaller than a predetermined threshold (such as 2 kV or smaller), for example, it is determined that the radiation doses are the same. If the absolute value of the difference exceeds the threshold, it is determined that the radiation doses are different. In addition to the absolute value of the difference in tube voltage, the ratio of the tube voltage in the second exposure to the tube voltage in the first exposure may be used in the determination. With this arrangement, user-friendliness is increased.

Alternatively, the user may be prohibited from setting different radiation qualities for the first exposure and the second exposure, so that the above described process of determining whether there is a difference in radiation quality can be omitted. Specifically, when the imaging conditions for the first exposure and the second exposure are set, the two tube voltages are only allowed to be set at the same value. Also, when the imaging conditions for the first exposure and the second exposure are set, only the same settings can be set for the presence/absence of added filters and the types of the added filters in the first exposure and the second exposure. With this arrangement, the process of determining whether there is a difference in radiation quality is omitted, and only the processes for cases where radiation qualities are always the same are performed. That is, the process in step S102 described above is not performed. In this manner, the processing can be simplified, and the third exposure record can be displayed earlier. Normally, the radiographer checks whether the third exposure image and the third exposure record are the intended ones after the end of the main exposure, and then moves on to the next imaging operation. Accordingly, earlier display of the third exposure record leads to a reduction of unnecessary waiting time for the radiographer.

In the above embodiment, in the case of the combining exposure, the first exposure record and the second exposure record are added up under certain conditions, are then linked to the third exposure image, and are output and displayed. In the case of the non-combining exposure, the second exposure record is linked to the third exposure image, and is output and displayed. In this manner, the exposure record that has contributed to the image generation can be appropriately linked to the third exposure image. In other words, the exposure record of each image can be appropriately managed. On the other hand, some users prefer to consider the first exposure and the second exposure as a series of imaging processes, and manage the exposure records of the series of imaging processes. For such users, the above management of the exposure record of each image is inconvenient, and it is more appropriate to add up the exposure records of the series of the first exposure and the second exposure under certain conditions, and link the sum of the exposure records to the third exposure image before output and display, regardless of whether the first exposure image and the second exposure image has been combined. Specifically, the control unit 31 does not determine to combine the pre-exposure image and the main exposure image in step S101 in FIG. 7, but always performs the same process as that in the case where the pre-exposure image and the main exposure image are combined (step S101, YES). Steps S102 and the steps that follow are the same as those in the above embodiment. With this arrangement, whether or not the pre-exposure image and the main exposure image are combined, the third exposure record, which is the sum of the first exposure record and the second exposure record, is linked to the third exposure image, and is output and displayed, under predetermined conditions. As a result, the user can manage the exposure record of each imaging operation.

Alternatively, the exposure record of each imaging operation may be managed, while the user is prohibited from setting different radiation qualities for the first exposure and the second exposure so that the above described process of determining whether there is a difference in radiation quality can be omitted. In this case, the processes in steps S101 and S102 can be omitted, the processing can be further simplified, and the display of the third exposure record can be made even earlier. As a result, unnecessary waiting time of the radiographer can be reduced.

Further, in the above embodiment, the control unit 31 is designed to serve as the totalizer, the linker, and the selector. However, embodiments of the present invention are not limited to this, and the totalizer, the linker, and the selector may be formed separately from one another.

Further, in the above embodiment, the console 3 has been described as an example of the exposure record totalizer. However, embodiments of the present invention are not limited to this, and the exposure record totalizer may be provided outside the radiography system 100.

Although embodiments of the present invention have been described and illustrated in detail, the disclosed embodiments are made for purposes of illustration and example only and not limitation. The scope of the present invention should be interpreted by terms of the appended claims. That is, the present invention can be embodied in various forms, without departing from its scope or principal features.

What is claimed is:

1. An exposure record totalizer comprising:
a hardware processor that receives a first exposure record which is an actual exposure record of a first exposure and a second exposure record which is an actual exposure record of a second exposure, when a radiography system generates a first exposure image through the first exposure and a second exposure image through the second exposure, the first exposure record including a first parameter with a first value, the second exposure record including the first parameter with a second value, the first parameter being at least one of an irradiation time, a tube current time product, an area dose value and an incident surface dose value;
that combines the first exposure record and the second exposure record to generate a third exposure record, the third exposure record including the first parameter with a third value, the third value being a total of the first value and the second value;
that links information about the third exposure record to a third exposure image generated on the basis of the first exposure image and the second exposure image; and
that displays, on a display, the third exposure image and the third exposure record.

2. A radiography system comprising:
an irradiator that emits radiation;
a radiographic imager that generates image data of an exposure image by receiving the radiation; and
the exposure record totalizer according to claim 1.

3. The exposure record totalizer according to claim 1, wherein,
the first exposure record includes a second parameter with a fourth value,
the second exposure record includes the second parameter with a fifth value,
the second parameter is at least one of a tube voltage and a tube current of radiation, and
the third exposure record includes the second parameter with a sixth value, the sixth value being identical to one of the fourth value and the fifth value.

4. An exposure record totalizer comprising:
a hardware processor that receives a first exposure record which is an actual exposure record of a first exposure and a second exposure record which is an actual exposure record of a second exposure according to predetermined conditions, when a radiography system generates a first exposure image through the first exposure and a second exposure image through the second exposure, the first exposure record including a first parameter with a first value, the second exposure record including the first parameter with a second value, the first parameter being at least one of an irradiation time, a tube current time product, an area dose value and an incident surface dose value;

that combines the first exposure record and the second exposure record to generate a third exposure record, the third exposure record including the first parameter with a third value, the third value being a total of the first value and the second value;

that links information about the third exposure record to a third exposure image generated on the basis of the first exposure image and the second exposure image; and that displays, on a display, the third exposure image and the third exposure record.

5. The exposure record totalizer according to claim 4, wherein
the hardware processor outputs the third exposure image.

6. The exposure record totalizer according to claim 4, wherein,
when the first exposure image and the second exposure image are not combined, the hardware processor determines not to add up the first exposure record and the second exposure record.

7. The exposure record totalizer according to claim 4, wherein
the hardware processor selects either combining exposure to combine the first exposure image and the second exposure image into the third exposure image, or non-combining exposure to set one of the first exposure image and the second exposure image as the third exposure image while not combining the first exposure image and the second exposure image.

8. The exposure record totalizer according to claim 7, wherein
the hardware processor selects either the combining exposure or the non-combining exposure, on the basis of information about body movement of an object of the radiography system.

9. The exposure record totalizer according to claim 7, further comprising
a manipulator that outputs a selection command for either the combining exposure or the non-combining exposure to the hardware processor, on the basis of an operation performed by a user.

10. The exposure record totalizer according to claim 4, wherein,
when the hardware processor determines to add up the first exposure record and the second exposure record, the hardware processor sets an exposure record that is a sum of the first exposure record and the second exposure record, as the third exposure record.

11. The exposure record totalizer according to claim 4, wherein,
when the hardware processor determines not to add up the first exposure record and the second exposure record, the hardware processor sets one of the first exposure record and the second exposure record as the third exposure record.

12. The exposure record totalizer according to claim 4, further comprising
a display that displays information based on the third exposure record.

13. The exposure record totalizer according to claim 12, wherein,
when displaying a combined exposure image generated by combining the first exposure image and the second exposure image, the display displays the combined exposure image while not displaying the first exposure image and the second exposure image.

14. The exposure record totalizer according to claim 12, wherein,
when displaying a combined exposure image generated by combining the first exposure image and the second exposure image, the display displays the third exposure record while not displaying the first exposure record and the second exposure record.

15. The exposure record totalizer according to claim 12, wherein,
when displaying one of the first exposure image and the second exposure image, the display does not display the other one of the first exposure image and the second exposure image, and a combined exposure image generated by combining the first exposure image and the second exposure image.

16. The exposure record totalizer according to claim 12, wherein,
when displaying one of the first exposure image and the second exposure image, the display does not display an exposure record relating to the other one of the first exposure image and the second exposure image, and an exposure record relating to a combined exposure image generated by combining the first exposure image and the second exposure image.

17. The exposure record totalizer according to claim 12, wherein
the display simultaneously displays a combined exposure image generated by combining the first exposure image and the second exposure image, and the second exposure image.

18. The exposure record totalizer according to claim 17, wherein
the display displays information based on the third exposure record and information based on the second exposure record, while simultaneously displaying the combined exposure image and the second exposure image.

19. The exposure record totalizer according to claim 4, wherein,
the hardware processor determines whether to add up the first exposure record and the second exposure record, when the first exposure image and the second exposure image are combined, and
adds up the first exposure record and the second exposure record when determining to add up the first exposure record and the second exposure record.

20. The exposure record totalizer according to claim 19, wherein,
when the first exposure image and the second exposure image are combined, the hardware processor determines whether to add up the first exposure record and the second exposure record, depending on whether radiation quality differs between the first exposure and the second exposure.

21. The exposure record totalizer according to claim 20, wherein, when the radiation quality is the same between the first exposure and the second exposure, the hardware processor determines to add up the first exposure record and the second exposure record.

22. The exposure record totalizer according to claim 20, wherein, when the radiation quality differs between the first exposure and the second exposure, the hardware processor determines not to add up the first exposure record and the second exposure record.

23. A radiography system comprising:

an irradiator that emits radiation;

a radiographic imager that generates image data of an exposure image by receiving the radiation; and the exposure record totalizer according to claim 4.

24. The exposure record totalizer according to claim 4, wherein, the first exposure record includes a second parameter with a fourth value, the second exposure record includes the second parameter with a fifth value, the second parameter is at least one of a tube voltage and a tube current of radiation, and the third exposure record includes the second parameter with a sixth value, the sixth value being identical to one of the fourth value and the fifth value.

* * * * *